United States Patent
Swedo et al.

(10) Patent No.: US 7,939,589 B2
(45) Date of Patent: May 10, 2011

(54) POLYHYDROXY-DIAMINES AS LOW ODOR, LOW VOC MULTI-FUNCTIONAL ADDITIVES FOR PAINTS AND COATINGS

(75) Inventors: Raymond J. Swedo, Mount Prospect, IL (US); Esin Busche, Naperville, IL (US); John W. Quinn, Skokie, IL (US)

(73) Assignee: Angus Chemical Company, Buffalo Grove, IL (US)

( * ) Notice: Subject to any disclaimer, the term of this patent is extended or adjusted under 35 U.S.C. 154(b) by 0 days.

(21) Appl. No.: 12/817,771

(22) Filed: Jun. 17, 2010

(65) Prior Publication Data

US 2010/0326320 A1    Dec. 30, 2010

Related U.S. Application Data

(60) Provisional application No. 61/220,601, filed on Jun. 26, 2009.

(51) Int. Cl.
*C08K 5/17*  (2006.01)
*C07C 211/01*  (2006.01)
(52) U.S. Cl. ............ 524/249; 564/461; 564/507
(58) Field of Classification Search .......... 524/249; 564/461, 507
See application file for complete search history.

(56) References Cited

U.S. PATENT DOCUMENTS

| | | | |
|---|---|---|---|
| 2,046,720 A * | 7/1936 | Bottoms | 564/478 |
| 2,393,825 A | 1/1946 | Senkus et al. | |
| 2,408,096 A * | 9/1946 | Pierce et al. | 564/507 |
| 3,098,097 A * | 7/1963 | Jenny et al. | 564/507 |
| 3,491,149 A * | 1/1970 | Brake | 564/461 |
| 3,959,378 A * | 5/1976 | Eckert | 564/507 |
| 7,462,746 B2 * | 12/2008 | Petasis et al. | 564/507 |

FOREIGN PATENT DOCUMENTS

WO    2008081036    7/2008

OTHER PUBLICATIONS

Senkus, "Reaction of Primary Aliphatic Amines with Formaldehyde and Nitroparaffins", Journal of the American Chemical Society, 1946, pp. 10-12, vol. 68.

* cited by examiner

*Primary Examiner* — Milton I Cano
*Assistant Examiner* — John Uselding

(57) ABSTRACT

Provided are polyhydroxy-diamine compounds for use as neutralizing agents for paints and coatings. The compounds are of the formula (I):

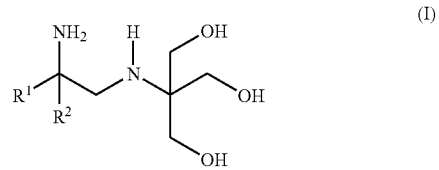

wherein $R^1$ and $R^2$ are as defined herein.

10 Claims, No Drawings

POLYHYDROXY-DIAMINES AS LOW ODOR, LOW VOC MULTI-FUNCTIONAL ADDITIVES FOR PAINTS AND COATINGS

This application claims priority to U.S. provisional application Ser. No. 61/220,601, filed Jun. 26, 2009, which is incorporated herein by reference in its entirety.

FIELD OF THE INVENTION

The invention relates to polyhydroxy-diamine compounds and their use as low odor, low volatile organic content (VOC) additives for paints and coatings.

BACKGROUND OF THE INVENTION

Organic amines are used in aqueous based paints as neutralizing agents. In many geographies, paint manufacturers are facing regulations to reduce the volatile organic content (VOC) of their formulations. Most conventional neutralizing amines are 100% volatile and are therefore VOC contributors. In addition, when used in an otherwise low VOC paint formulation, the odor of such amines is more noticeable.

Ammonia and inorganic hydroxides are potential alternatives for use as neutralizers, that are by definition non-VOC contributors. However, ammonia, while an efficient neutralizer, has a very strong odor and is therefore unsuitable for use in low odor paint. Inorganic hydroxides, such as potassium hydroxide, are undesirable because they often result in coatings with poor scrub resistance.

Accordingly, efficient neutralizing agents, which both exhibit low or no VOC and have very low or no amine odor, would be a significant advance for the paints and coatings industry.

BRIEF SUMMARY OF THE INVENTION

In one aspect, the invention provides low VOC and low odor polyhydroxy-diamine compounds that are useful as neutralizing agents for aqueous based paints and coatings.

The compounds of the invention are of the formula (I):

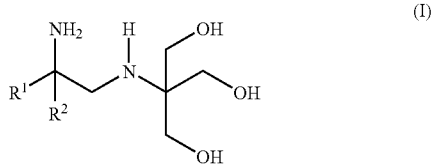

or salt thereof, wherein $R^1$ and $R^2$ are as defined herein.

In another aspect, the invention provides an aqueous based paint or coating comprising a compound of formula (I) as the neutralizing agent.

In a further aspect, the invention provides a method for reducing the volatile organic compound content of an aqueous based paint or coating containing a neutralizing agent, a binder, a carrier, and a pigment. The method comprises using, as the neutralizing agent in the paint or coating an effective amount of a compound of formula (I).

DETAILED DESCRIPTION OF THE INVENTION

As noted above, the invention provides polyhydroxy-diamine compounds that are useful as neutralizing agents in aqueous-based paint and coating formulations. Neutralizing agents are included in such formulations to raise the pH to a desired value, typically between about 8 and 10. Most conventional neutralizing agents currently used in the industry are VOC contributors. In addition, when used in an otherwise low VOC formulation, the odor of conventional neutralizing agents is more noticeable.

In contrast, the compounds of the invention are excellent low odor materials with the benefit of having very low VOC. For instance, 2-(2-amino-2-methylpropylamino)-2-(hydroxymethyl)propane-1,3-diol, an exemplary compound of the invention, exhibits a VOC contribution of 3.9%, whereas 2-methyl-2-amino-propanol, a conventional neutralizing agent, exhibits a VOC contribution of 100%.

In addition to their excellent low VOC and low odor attributes, the compounds of the invention impart comparable performance properties to those provided by conventional neutralizing amines. Consequently, the advantages of low odor and low VOC are achieved with the compounds of the invention, without significant impact on other attributes of the paint or coating. Further, the compounds of the invention are effective co-dispersants for pigment particles present in paint and coating formulations, thus serving dual roles in the formulation and consequently again conserving materials.

The compounds of the invention are of the formula (I):

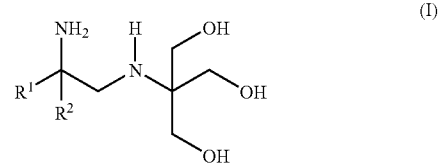

wherein $R^1$ and $R^2$ are independently $C_1$-$C_{10}$ alkyl, or $R^1$ and $R^2$, together with the carbon to which they are attached, form a $C_3$-$C_{12}$ cycloalkyl ring optionally substituted with $C_1$-$C_6$ alkyl.

In one embodiment, $R^1$ in the compounds of formula I is $C_1$-$C_3$ alkyl. In a further embodiment, $R^1$ is methyl.

In one embodiment, $R^2$ in the compounds of formula I is $C_1$-$C_3$ alkyl. In a further embodiment, $R^2$ is methyl.

In one embodiment, $R^1$ is $C_1$-$C_3$ alkyl and $R^2$ is $C_1$-$C_3$ alkyl.

In one embodiment, $R^1$ and $R^2$ in the compounds of formula I, together with the carbon to which they are attached, form a $C_3$-$C_{12}$ cycloalkyl ring. In a further embodiment, $R^1$ and $R^2$ form a $C_5$-$C_8$ cycloalkyl ring. The ring is optionally substituted with 1 or 2 $C_1$-$C_6$ alkyl substituents, such as groups independently selected from methyl, ethyl, and propyl.

In one embodiment, the compound of formula I is 2-(2-amino-2-methylpropylamino)-2-(hydroxymethyl)propane-1,3-diol (i.e., $R^1$ and $R^2$ in formula I are both methyl).

In one embodiment, the compound of formula I is 2-((1-aminocyclohexyl)methylamino)-2-(hydroxymethyl)propane-1,3-diol (i.e., $R^1$ and $R^2$ and the carbon to which they are attached form a cyclohexyl ring).

Compounds of formula I may be prepared by the Mannich reaction of tris (hydroxymethyl)aminomethane with a nitroalcohol of the formula:

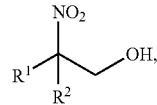

followed by reduction of the nitro group of the product to an amine via hydrogenation in the presence of a hydrogenation catalyst. The Mannich reaction is typically conducted under inert atmosphere and in the presence of a diluent, such as water, methanol, or both. The hydrogenation step is generally carried out in a reactor pressurized with hydrogen gas, again typically in the presence of a diluent, such as methanol. Suitable hydrogenation catalysts include Raney nickel.

Alternatively, compounds of formula I may be prepared by the in situ Mannich reaction of tris(hydroxymethyl)aminomethane with a mixture of the corresponding nitroparaffin and formaldehyde followed by reduction of the nitro group of the product to an amine via hydrogenation in the presence of a hydrogenation catalyst.

In a second aspect, the invention provides an aqueous based paint or coating in which a compound of formula (I) is present as a neutralizing agent. The paint or coating is used to provide a protective and/or decorative barrier for residential and industrial surfaces, such as for floors, automobiles, exteriors and interiors of houses, and other buildings. According to this aspect of the invention, the paint or coating formulation, in addition to comprising a neutralizing agent, also comprises a binder, a pigment, and a carrier.

Pigments are included to provide hiding power and the desired color to the final coated material and may also be used to provide bulk to the paint or coating. While multiple pigments may be present in end-use paints or coatings, sometimes only white pigment, such as titanium oxide, perhaps in combination with extender pigments such as calcium carbonate and/or kaolin clay, is added in the early stages of the formation of the formulation. Any other desired pigments of various colors (including more white pigment) can optionally be added at the later stages of, or after, the formulation is completed.

Pigments may be organic or inorganic. Examples of pigments can include, but are not limited to, titanium dioxide, kaolin clay, calcined kaolin clay, carbon black, iron oxide black, iron oxide yellow, iron oxide red, iron oxide brown, organic red pigments, including quinacridone red and metallized and non-metallized azo reds (e.g., lithols, lithol rubine, toluidine red, naphthol red), phthalocyanine blue, phthalocyanine green, mono- or di-arylide yellow, benzimidazolone yellow, heterocyclic yellow, quinacridone magenta, quinacridone violet, and the like, and any combination thereof.

Binders are included in the paint and coating formulations to provide a network in which the pigment particles are dispersed and suspended. Binders bind the pigment particles together and provide integrity and adhesion for the paint or coating film. Generally, there are two classes of binders: latex binders are used in aqueous based formulations, and alkyd-based binders are used in non-aqueous formulations, ultimately resulting in latex paints and coatings and alkyd paints and coatings, respectively.

In latex based paint and coating formulations, the binders are typically prepared by free radical initiated aqueous emulsion polymerization of a monomer mixture containing alkyl acrylate (methyl acrylate, ethyl acrylate, butyl acrylate and/or 2-ethylhexylacrylate), alkyl methacrylate, vinyl alcohol/acetate, styrene, and/or acrylonitrile and ethylene type monomers. Preferred binders include acrylic, vinyl acrylic, styrenated-acrylic, or vinyl acetate ethylene based materials. The amount of the binder in the formulations of the invention can be the amount conventionally used in paint and coating formulations, which can vary widely due to the desired gloss/sheen range, and also the solids concentration, of a specific paint formulation. By way of non-limiting example, the amount of binder solids can be from about 5% to about 25% of the total formula volume.

The formulations also contain a carrier in which the formulation ingredients are dissolved, dispersed, and/or suspended. In the aqueous based formulations of the invention, the carrier is usually water, although other water-based solutions such as water-alcohol mixtures and the like may be used. The aqueous carrier generally makes up the balance of the formulation, after all the other ingredients have been accounted for.

Other additives may be included in the paint and coating formulations besides the neutralizing agents, pigments, binders, and carriers discussed above. These include, but are not limited to, leveling agents and surfactants, thickeners, rheology modifiers, co-solvents such as glycols, including propylene glycol or ethylene glycol, corrosion inhibitors, defoamers, co-dispersants, additional aminoalcohol compounds, and biocides.

The paint and coating formulations of the invention may be manufactured by conventional paint manufacturing techniques, which are well known to those skilled in the art. Typically, the formulations are manufactured by a two-step process. First, a dispersion phase, commonly referred to as the grind phase, is prepared by mixing the dry pigments with other grind phase components, including most other solid powder formulation materials, under constant high shear agitation to provide a high viscosity and high solids mixture. This part of the process is designed to effectively wet and dis-agglomerate the dry pigments and stabilize them in an aqueous dispersion.

The second step of the paint manufacturing process is commonly referred to as the letdown or thindown phase, because the viscous grind is diluted with the remaining formulation components, which are generally less viscous than the grind mix. Typically, the binders, any predispersed pigments, and any other paint materials that only require mixing and perhaps moderate shear, are incorporated during the letdown phase. The letdown phase may be done either by sequentially adding the letdown components into a vessel containing the grind mix, or by adding the grind mix into a vessel containing a premix of the latex resins and other letdown components, followed by sequential addition of the final letdown components. In either case, constant agitation is needed, although application of high shear is not required. The neutralizing agent compounds of the invention are typically added to the formulation at one or more of three different places in the manufacturing process: to the pigment dispersion, to the binder dispersion, and/or in a final addition to the paint formulation. The amount used is determined based on the desired pH of the formulation. Typically, an amount of the compound is added so as to provide a final pH in the range of about 8 and 10, more preferably about 8.5 to 9.5.

In a further aspect, the invention provides a method for reducing the volatile organic compound content of an aqueous based paint or coating that contains a neutralizing agent, a binder, a carrier, and a pigment. The method comprises using as the neutralizing agent an effective amount of a compound for formula (I). As noted above, an effective amount is the quantity required to provide a pH of about 8 to 10, preferably 8.5 to 9.5, in the paint or coating formulation.

The term "alkyl" as used herein, means a straight or branched chain hydrocarbon containing the indicated number of carbon atoms. If no number is indicated, then alkyl contains from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "cycloalkyl" as employed herein includes saturated and partially unsaturated cyclic hydrocarbon groups having 3 to 12 carbons, preferably 5 to 8 carbons. Preferred cycloalkyl groups include, without limitation, cyclopropyl, cyclobutyl, cyclopentyl, cyclopentenyl, cyclohexyl, cyclohexenyl, cycloheptyl, and cyclooctyl.

Unless otherwise indicated, ratios, percentages, parts, and the like used herein are by weight.

The following examples are illustrative of the invention but are not intended to limit its scope. Unless otherwise indicated, ratios, percentages, parts, and the like used herein are by weight.

EXAMPLES

Example 1

Synthesis of 2-(Hydroxymethyl)-2-(2-methyl-2-nitropropylamino)propane-1,3-diol (TA-NMP)

A 2-L 3-neck flask is equipped with a mechanical stirrer, a reflux condenser with nitrogen blanket, and a heating mantle with a temperature controller and a thermocouple. The flask is charged with 238.3 grams (2.0 moles) of 2-methyl-2-nitropropanol (NMP), 242.4 grams (2.0 moles) of tris (hydroxymethyl)aminomethane (TA), and 200 grams of water. The mixture is stirred under nitrogen. An endotherm to <10° C. is observed; the temperature increases as the bulk of the solids dissolve. The clear, colorless solution is then maintained at 30° C. After a few hours, the mixture becomes turbid; later, crystalline solids begin to separate out. After about 11 hours at 30° C., it is no longer possible to stir the mixture. The mixture is maintained at room temperature overnight, then the solids are collected on a glass frit filter. The crystalline product is dried in air and then in a vacuum oven at 55° C. for several hours. The yield of product is 278.1 grams (62.3%). The melting point is 95-97° C. A second crop of crystals is similarly isolated from the initial filtrate. After drying, this gives an additional 33.3 grams of product. The melting point is 94-98° C. The two crops are combined to give a total product yield of 311.4 grams (70.1%). LC analysis shows a product purity of >92%, with about 2.5% residual NMP present. IR, $^1$H- and $^{13}$C-NMR analyses are consistent with the desired structure.

Example 2

Synthesis of 2-(2-Amino-2-methylpropylamino)-2-(hydroxymethyl)propane-1,3-diol (TA-AMP)

A 2-L 316 stainless steel Parr reactor is charged with 135 grams (0.61 moles) of TA-NMP, 500 mL of methanol, and 16.4 grams of water wet RaNi 3111 catalyst. The reactor is flushed with nitrogen, then pressurized with hydrogen. The reduction is conducted at 300 psig hydrogen at 40° C. The reduction is complete in about 1.5 hours. The reactor mixture is filtered to remove the catalyst; the filtrate is clear and pale blue in color. The methanol and water are removed from the filtrate by rotary evaporation to give 118 grams (100%) of viscous oil which crystallizes on standing. MP=73-75° C. GC analysis shows 91% TA-AMP, with about 9.1% of residual starting materials and/or byrproducts. GC/MS, IR, $^1$H- and $^{13}$C-NMR analyses are consistent with the desired structure.

Titration gives $pK_1$=9.9 and $pK_2$=4.8. Volatility by the modified EPA Test Method 24 (described below) is 3.9%.

Example 3

Synthesis of 2-((1-nitrocyclohexyl)methylamino)-2-(hydroxymethyl)propane-1,3-diol (TA-NCyHM)

A 1-L 3-neck flask is equipped with a mechanical stirrer, a reflux condenser with nitrogen blanket, and a heating mantle with a temperature controller and a thermocouple. The flask is charged with 127.4 grams (0.8 moles) of (1-nitrocyclohexyl) methanol (NCyHM), with 96.9 grams (0.8 moles) of TA, with 50 mL of methanol, and with 50 mL of water. The mixture is stirred under nitrogen until the solids dissolve, then the clear solution is warmed to 45° C. After about 4 hours at 45° C., an oil phase begins to separate, and after 12 hours the oil becomes a waxy solid. After 19 hours at 45° C., the reaction mixture is an off-white paste that is too difficult to stir. The reaction mixture is left to stand at room temperature for 10 days, then the solids are collected on a glass frit filter. The solids are washed on the filter with portions of hexanes. After drying, the yield of TA-NCyHM product is 171.9 grams (82%). Melting point is 110-113° C. LC analysis show a product purity of >91%, with 6.4% of mono-oxazolidine by-product. LC/MS, IR,
$^1$H- and $^{13}$C-NMR analyses are consistent with the desired structure.

Example 4

Synthesis of 2-((1-aminocyclohexyl)methylamino)-2-(hydroxymethyl)propane-1,3-diol (TA-ACyHM)

A 2-L 316 stainless steel Parr reactor is charged with 100 grams (0.38 moles) of TA-NCyHM, 500 mL of methanol, and 25.3 grams of water wet RaNi 3111 catalyst. The reactor is flushed with nitrogen, then pressurized with hydrogen. The reduction is conducted at 300 psig hydrogen at 40° C. The reduction is complete in about 1.5 hours.

The reactor mixture is filtered to remove the catalyst; the filtrate is clear and pale yellow. The methanol and water are removed from the filtrate by rotary evaporation to give 80.6 grams of an off-white paste product. GC analysis shows this product to contain nearly 20% of residual TA. This product is mixed with 500 mL of ethyl acetate, and the mixture is heated to reflux for about 15 minutes. The mixture is cooled to room temperature, then it is filtered free of the TA solids. The solids are washed on the filter with ethyl acetate, then the combined filtrate and washings are solvent stripped by rotary evaporation to give 67.7 grams (76%) of TA-ACyHM as a very viscous oil. GC analysis shows a product purity of >98%, with traces of cyclohexylamine, 1-aminocyclohexanemethanol (ACyHM), and oxazolidine byproduct. GC/MS, IR, $^1$H- and $^{13}$C-NMR analyses are consistent with the desired structure. Titration gives $pK_1$=9.7 and $pK_2$=4.5. Volatility by the modified EPA Test Method 24 is 3.8%.

Example 5

Syntheses of Mannich Products Via Nitroparaffins

N-(2-Nitroisobutyl)tris(hydroxymethyl)aminomethane (TA-NMP). A 500 mL 3-neck flask is equipped with a magnetic stirrer, a reflux condenser with nitrogen blanket, an addition funnel, and a heating mantle with a temperature controller and a thermocouple. The flask is charged with 2-nitropropane (89.11 grams, 1.0 mole), TA (121.21 grams, 1.0 mole), 2 mL of an 80% solution of 2-dimethylamino-2-methyl-1-propanol (available as DMAMP-80™ from The Dow Chemical Company), and water (50 mL). The mixture is heated to 50° C. while stirring under nitrogen. A clear, yellow solution is obtained. The funnel is charged with methyl Formcel (54.8 grams, 1.0 mole). The Formcel is added to the amine-nitroparaffin mixture over a period of about 1½ hours. No exotherm is noted. After completing the addition, the reaction mixture temperature is increased to 55° C. This temperature is maintained for 4 hours, during which time solids begin to separate. The reaction mixture is cooled to room temperature, and the solids are collected by filtration onto a glass frit funnel. The solids are washed on the filter with small portions of water, then they are dried. The yield of white crystalline product is 160.9 grams (72%). MP=92-94° C. Product structure is confirmed by IR, NMR, and LC/MS analyses. LC/MS analysis shows the presence of some oxazolidine derived from the expected Mannich product, but this is not detected by NMR.

2-((Hydroxymethyl)-2-(1-nitrocyclohexyl)methylamino) propane-1,3-diol (TA-NCyHM). A 500 mL 3-neck flask is equipped with a magnetic stirrer, a reflux condenser with nitrogen blanket, an addition funnel, and a heating mantle with a temperature controller and a thermocouple. The flask is charged with the TA (121.25 grams, 1.0 mole), nitrocyclohexane (NcyH; 129.21 grams, 1.0 mole), DMAMP-80™ (2 mL), and with water (50 mL). The funnel is charged with methyl Formcel (54.8 grams, 1.0 mole). The yellow, multiphase amine-nitroparaffin mixture is stirred under nitrogen and is heated to 50° C. The Formcel is added to this mixture over a period of about 1 hour. No exotherm is noted. After completing the addition, the reaction mixture is heated to 55° C. for a total of about 5 hours, during which time solids begin to separate out. The reaction mixture is cooled to room temperature, and the solids are collected by filtration onto a glass frit funnel. The solids are washed on the filter with small portions of water, then they are dried to give 174.0 grams of white crystalline product (66%). MP=112-115° C. LC analysis showed >94% product. Product structure is confirmed by IR, NMR, and LC/MS analyses. A small amount of oxazolidine is detected in the LC/MS analysis, but was not seen in the NMR analyses.

Example 6

Evaluation of TA-AMP and TA-ACyHM as Neutralizing Agent and Co-Dispersants in Semi-Gloss Latex Paint The TA-AMP and TA-AcyHM compounds are tested as neutralizing, co-dispersing amines and compared relative to commercial neutralizers in an aqueous based, latex semi-gloss formulation. This paint formulation is a conventional semi-gloss latex paint that does not meet the low-VOC definition of less than 50 g/L.

The comparative neutralizers are as follows:

2-Amino-2-methyl-1-propanol (AMP): available from ANGUS Chemical Company as AMP-95®.

2-Amino-2-ethyl-1,3-propane-diol (AEPD): available from ANGUS as AEPD™ VOX 1000.

N-Butyl-diethanolamine (NBDA): available from Taminco as Vantex®-T.

The paint formulation in which the compounds are tested is latex based semi-gloss material containing:

Pigments such as titanium dioxide (e.g., TiPure® R942 from DuPont) and ground calcium carbonate (e.g., Omyacarb® UF from Omya, Inc.) (total of both pigments 20-25%).

Binder such as UCAR™ Latex 379 and 6030 from The Dow Chemical Company (total of both binders 40-45%).

Thickeners and rheology modifiers such as hydroxyethylcellulose (e.g., Cellosize™ HEC from Dow) and solvent-free, non-ionic associative thickening agent/hydrophobically modified polyethylene oxide urethane-HEUR (Acrysol™ RM-5000 from Rohm and Haas) (total of both thickener (3-5%).

Neutralizer or amine (comparative or inventive) are tested on a equimolar basis. For AMP, the concentration based on the total formulation is 0.18 weight percent.

The formulation for testing of the amines is shown in Table 1:

TABLE 1

Semi-gloss formula for equimolar comparison of organic amine neutralizers

| | AMP[2] | TA-AMP[1] | TA-ACyHM[1] | AEP[2] | NBDA[2] |
|---|---|---|---|---|---|
| Water | 140.00 | 140.00 | 140.00 | 140.00 | 140.00 |
| Cellosize™ QP-300, HEC thickener | 5.00 | 5.00 | 5.00 | 5.00 | 5.00 |
| Water | 10.00 | 10.00 | 10.00 | 10.00 | 10.00 |
| Canguard BIT 20 Biocide, | 0.50 | 0.50 | 0.50 | 0.50 | 0.50 |
| Tamol 1124 dispersant | 5.00 | 5.00 | 5.00 | 5.00 | 5.00 |
| Triton CF-10 surfactant | 2.00 | 2.00 | 2.00 | 2.00 | 2.00 |
| Triton GR-5M surfactant | 0.50 | 0.50 | 0.50 | 0.50 | 0.50 |
| Drew plus Y-381 defoamer | 1.00 | 1.00 | 1.00 | 1.00 | 1.00 |
| Ethylene Glycol | 30.00 | 30.00 | 30.00 | 30.00 | 30.00 |
| AMP amine | 1.90 | — | — | — | — |
| TA-AMP amine | — | 4.10 | — | — | — |
| TA-ACyHM amine | — | — | 4.95 | — | — |
| AEPD amine | — | — | — | 2.54 | — |
| NBDA amine | — | — | — | — | 3.44 |
| Omycarb UF ground calcium carbonate | 25.00 | 25.00 | 25.00 | 25.00 | 25.00 |
| Water | 20.00 | 20.00 | 20.00 | 20.00 | 20.00 |
| UCAR ™ Latex 379G (vinyl acrylic latex) | 375.00 | 375.00 | 375.00 | 375.00 | 375.00 |
| UCAR ™ Latex 6030 (acrylic latex) | 47.00 | 47.00 | 47.00 | 47.00 | 47.00 |
| Butyl Carbitol coalescent | 6.00 | 6.00 | 6.00 | 6.00 | 6.00 |

TABLE 1-continued

Semi-gloss formula for equimolar comparison of organic amine neutralizers

|  | AMP[2] | TA-AMP[1] | TA-ACyHM[1] | AEP[2] | NBDA[2] |
|---|---|---|---|---|---|
| Archer RC reactive coalescent | 12.00 | 12.00 | 12.00 | 12.00 | 12.00 |
| Drew plus Y-381 defoamer | 1.50 | 1.50 | 1.50 | 1.50 | 1.50 |
| TiPure ® R942 titanium dioxide slurry, 76.5% | 250.00 | 250.00 | 250.00 | 250.00 | 250.00 |
| Acrysol ™ RM-5000 thickener (HEUR-type) | 30.00 | 30.00 | 30.00 | 30.00 | 30.00 |
| Water | 64.14 | 61.94 | 61.09 | 63.50 | 62.60 |
| DREW Plus Y-381 defoamer | 1.50 | 1.50 | 1.50 | 1.50 | 1.50 |
| TOTAL | 1028.04 | 1028.04 | 1028.04 | 1028.04 | 1028.04 |
| Total Solids wt % | 46.2 | 46.2 | 46.2 | 46.2 | 46.2 |
| Pigment volume concentration, % (PVC) | 23 | 23 | 23 | 23 | 23 |

[1]compound of the invention
[2]comparative compound

The formulation pH, particle size, film opacity, gloss, film color, and film yellowing, and the VOC and $pK_a$ values of the neat neutralizers, are determined as follows:

Coating Optical Properties (Opacity, Color, and Gloss). Coatings of the formulations are applied using a Symyx coating station with a 7-mil gap applicator, onto Leneta opacity charts (Form 15-1, B#3713). The opacity, gloss at 60° and color of the dried films is measured using an automated color/gloss/thickness robot based on a Symyx XCM module. The color and opacity are measured using an Ocean Optics ISP-REF integrating sphere with a 0.4" sampling aperture connected by a fiber optic cable to an Ocean Optics USB 4000 Spectrometer. Measurements are performed with D65 illumination. This apparatus is located on the left arm of a Symyx Core Module Robot which enables the colorimeter to be moved onto the sample in multiple locations. For this study measurements are done on three separate areas on both the black and white parts of each Leneta paper. The meter calculates color parameters according to the CIE L*a*b* color system. Yellowness is reported here in terms of the b* (yellow-blue scale) parameter, where increasing positive values for b* indicate increasing yellowness. The meter also calculates opacity according to ASTM D 2805. The gloss is measured in accordance with ASTM D 523 using a BYK micro-Tri-gloss Meter. This instrument is attached to the right arm of the Symyx Core Module Robot, along with a plate gripper used to move the samples from the BenchCel sample hotel to the deck of the Module. Gloss is measured in three different spots on the coatings over both the white and black parts of the Leneta paper.

Particle Size Analysis. The particle size distribution in the formulations is measured using a Beckman Coulter LS-230 Particle Size Analyzer using a Micro-Volume Accessory. One drop of the formulation is added to approximately 20 mL of deionized water, and shaken well. This diluted solution is then added drop wise to the micro-volume accessory by pipet until the absorbance reading is at least 8%. The sample is stirred continuously during the measurement. Particle sizes from 0.04 to 2000 microns can be detected. The particle size distribution of a garnet standard with nominal particle size 35 microns is measured to be 36±15 microns.

pH Measurements. The formulation pH is measured using a Fisher Scientific Accumet 15 pH meter, equipped with a ThermoElectron Orion 9203BN combination pH electrode. Commercial pH buffers are used to calibrate the equipment before each use. The reported values are the average of three separate reading on each formulation, the probe is cleaned with DI water between each measurement.

Volatile Organic Content (VOC). VOC is measured following EPA Method 24. The amines are weighed in a pan and kept in an oven for 1 h at 105-110° C. The percent weight loss is reported as the VOC, corrected for the water content in the sample which can be measured by Karl Fisher Titration.

Film Yellowing. Film yellowing is measured after exposing the coated Leneta panels to an ultraviolet light source for 116 hours at 50° C., using a model QUV accelerated weathering apparatus, with UVB-313 light source. Color is remeasured as described above, and the b* parameter is again reported here as a measure of film yellowness.

$pK_a$. $pK_a$ is measured by titration with a hydrochloric acid titrant solution, using an automated titrator that monitors pH with a combination electrode. The titrator plots pH vs. volume of titrant added, and first determines the titration endpoint(s) of each amine as the volume of titrant added at the inflection point(s) of the curve. The titrator reports the amine $pK_a$ value as the pH value at which one-half of the endpoint titrant volume has been delivered, or in the case of multiple endpoints, multiple $pK_a$ values are determined using the midpoints between titration endpoints. The inventive amines tested in this example each have two $pK_a$ values, due to the two different amine groups in each compound's respective molecular structure. The data are shown in Table 2.

TABLE 2

|  | TA-AMP[1] | TA-AcyHM[1] | AMP[2] | AEPD[2] | NBDA[2] |
|---|---|---|---|---|---|
| Particle Size (micro m) | 0.583 | 0.636 | 0.640 | 0.620 | 0.622 |
| Formulation pH | 9.1 | 9.0 | 9.3 | 9.0 | 9.0 |
| Film Opacity | 96.5 | 96.2 | 96.8 | 96.9 | 96.9 |
| Gloss, 60° | 29 | 28.7 | 28.7 | 32.2 | 30.9 |

TABLE 2-continued

|  | TA-AMP[1] | TA-AcyHM[1] | AMP[2] | AEPD[2] | NBDA[2] |
| --- | --- | --- | --- | --- | --- |
| Film color (b*, yellownwess) | 0.93 | 1.04 | 0.77 | 0.85 | 0.84 |
| Film yellowing after 116 hr UV-B exposure (b*, yellownwess) | 1.69 | 1.65 | 1.39 | 1.68 | 1.64 |
| VOC | 3.9 | 3.8 | 100 | 19 | 21 |
| $pK_a$ | $pK_1$ 9.9 $pK_2$ 4.8 | $pK_1$ 9.7 $pK_2$ 4.5 | 9.7 | 8.8 | 9.0 |

[1] Compound of the invention.
[2] Comparative compound.

The data in Table 2 shows the following:

Particle Size: TA-ACyHM provides a slightly higher average particle size and TA-AMP a slightly smaller average particle size than AMP. The AEPD and NBDA are comparable to AMP.

Formulation pH: TA-AMP provides a similar formulation pH value to AMP, but that of TA-ACyHM is somewhat lower, as is that for AEPD and NBDA.

Film Opacity: Both of the inventive compounds provide opacity values comparable to that of AMP. Those for the AEPD and NBDA are higher.

Film Gloss: Both the inventive compounds provide gloss values comparable to that of AMP. Those for the AEPD and NBDA are slightly higher.

Film Color: The inventive compounds impart slightly higher initial yellowness than AMP. The AEPD and NBDA are comparable.

Film Yellowing: All of the tesed amino alcohols yellow slightly more than AMP after UV exposure. The inventive compounds are comparable to the AEPD and NBDA.

% VOC: Both of the inventive compounds have much lower % VOC values than AMP, AEPD and NBDA.

$pK_a$ Values: The first $pK_a$ values of both of the inventive compounds are higher than those of AEPD and NBDA, but similar to the $pK_a$ of AMP.

In general, the compounds of the invention perform comparable to the three commercial products, AMP, NBDA and AEPD, achieving good co-dispersion of the pigment (as represented by the particle size analysis) which translates into good film opacity and gloss measurements. In contrast to the commercial materials, however, the compounds of the invention contain less than 4% VOC, thus, contributing negligible VOC content to the paint formulation.

Example 7

Evaluation of TA-ACyHM as Neutralizing Agent and Co-Dispersants in a Low-VOC Semi-Gloss Latex Paint The TA-AcyHM compound is tested as a neutralizing, co-dispersing amine and compared relative to the commercial neutralizer AMP in an aqueous based latex semi-gloss formulation, that meets the low-VOC definition of less than 50 g/L. The level for each neutralizer is chosen to meet the formula pH specification of 8.5 to 9.5.

The composition of the tested paint formulation is shown in Table 3.

TABLE 3

Low-VOC Semi-gloss latex paint (24 PVC)

|  | AMP-95 ®[1] lbs/100 gal | TA-ACyHM[2] lbs/100 gal |
| --- | --- | --- |
| Water | 100.00 | 100.00 |
| Cellosize ™ QP-300 (thickener) | 1.50 | 1.50 |
| Canguard ™ BIT 20-AS (anti-microbial) | 0.50 | 0.50 |
| propylene glycol (glycol) | 10.00 | 10.00 |
| Tamol ™ 731A dispersant, 25% active (dispersant) | 7.00 | 7.00 |
| potassium tripolyphosphate (KTPP) (buffer) | 1.50 | 1.50 |
| Ecosurf ™ SA-9 surfactant (surfactant) | 2.00 | 2.00 |
| Drewplus ® Y-381 defoamer (defoamer) | 1.00 | 1.00 |
| amine active | 1.48 | 2.70 |
| TiPure ® R-902+ titanium dioxide (opacifier and pigment) | 225.00 | 225.00 |
| Polygloss ® 90 kaolin clay (clay) | 25.00 | 25.00 |
| Water | 30.00 | 30.00 |
| UCAR ™ Acrylic Latex (binder) | 425.00 | 425.00 |
| Water | 174.40 | 174.40 |
| Acrysol ™ RM 5000, HEUR thickener, 18.5% (thickener) | 30.00 | 30.00 |
| Drewplus ® Y-381 defoamer (defoamer) | 1.50 | 1.50 |
| Water | 8.97 | 7.75 |
| Total (lbs) | 1045.45 | 1045.45 |

[1] Comparative compound.
[2] Compound of the invention prepared as described above.

The pH, low (KU) and high-shear ("ICI") viscosities, film opacity, film gloss, film yellowing, amine $pK_a$ value, amine % VOC, and amine odor of the formulations containing the tested compounds are determined as follows.

pH, Low Shear and High Shear Viscosity. The pH of each formulation is measured with a Corning Model 430 pH meter with a ceramic-junction probe. Krebs-units (KU) viscosity is measured with a Stormer viscometer with a stroboscopic timer (ASTM D562), at 24±1° C. The high shear ("ICI") viscosity is measured according to ASTM D 4287 using a Brookfield CAP 1000+ viscometer at a shear rate of 12,000 $s^{-1}$ at 900 rpm, with a 0.45° cone of radius 1.511 cm, and a sample temperature controlled at 25° C.

Gloss at 60° C., Opacity, and Yellowing. Color and gloss measurements are done on films applied with a 3-mil wet-film drawdown bar to Leneta Form 3-B opacity charts. Additional drawdowns are made from the heat-aged stability samples after 2 weeks at 60° C. Panels are dried at least 24 hours at room temperature before measurement.

Color measurements are done with a BYK-Gardner Color Guide Sphere color meter (D65 source/10° observer), which measures reflectance spectra in conformity to ASTM E 1164. The meter calculates color parameters according to the CIE L*a*b* color system. Yellowness is reported here in terms of the b* (yellow-blue scale) parameter.

Gloss at 60° is measured with a BYK-Gardner micro-TRI-gloss meter in accordance with ASTM D 523.

Scrub Resistance. Wet-scrub resistance is measured with a Gardco-Model D10 washability, wear, and friction tester, with a fixed speed of 37 cycles/minute according to ASTM D 2486. Replicate side-by-side drawdowns are drawn on Leneta P-121-10N black plastic panels with the 7-mil gap side of a U-shaped applicator bar (the Dow latex bar, available from Paul N. Gardner, Inc.). The panels are dried 7 days at 50% relative humidity at 25° C. The panels are secured to the stage of the scrub tester with shims under each of the side-by-side films to give a raised test area. Before each 400 cycles of the test, 10 g of the specified abrasive medium and 5 mL of water are placed in the path of the scrub brush. The end point for each paint film is recorded when the brush wears a continuous line of complete paint removal across the width of the raised test surface.

Wet adhesion. Wet adhesion test method is similar to ASTM D 6900, with the same test apparatus as for scrub resistance (ASTM D 2486). Leneta P-121-10N panels pre-coated with blue alkyd paint and dried at least three weeks serve as the test substrate. Side-by-side drawdowns of the latex test paint and reference paint are applied with the 7-mil gap of the Dow Latex bar, and dried one day at 50% relative humidity at 25° C. A razor-blade is used to make X-cuts through approximately 2½×1½-inch areas of the reference and test paint surfaces. Panels are immersed in water for 30 minutes and tested immediately for 500 cycles on the scrub tester over the cut surfaces of the paint. No abrasive scrub medium is used, and rather than inserting shims, the test panel is laid flat on the stage of the scrub machine. Results are reported as cycles to complete removal, or as percent removal after 500 cycles.

Blocking Resistance. Blocking is measured according to ASTM D 4946 at room temperature and at 50° C. Films of 3-mil wet-film thickness applied to opacity charts are dried for 1 and 3 days at 50% relative humidity at 25° C. before testing. For each test, coated panels are cut into triplicate pairs of 1½ inch squares. Each pair of squares is placed face to face, then each pair is covered with a No. 8 rubber stopper. A 1 kg weight is placed on the rubber stopper. The 50° C. oven tests are conducted for 30 minutes. At the end of each time period, the weights are removed and the pairs of squares are peeled apart with slow, steady force. The amount of adhesion is observed and evaluated on a scale of 0 (greatest adhesion) to 10 (least adhesion).

Color Acceptance Samples of each test paint in ½-pint cans are tinted with phthalo blue, dispensed by weight to yield the equivalent of two ounces volume of tint to gallon of white paint. These tinted paints are mixed approximately 90 seconds with a model 5400 paint shaker (Red Devil Equipment). Initial drawdowns of 3-mil wet-film thickness are drawn immediately on form 3-B opacity charts. Stability of the tinted paints is tested by rolling the ½ pint cans seven days on a roller mill which turns the cans at approximately 230 rpm. An additional set of drawdowns is made after removal of the samples from the roller. Colors of the initial panels, including the rubbed areas, and of the stability-tested samples are measured with over the white-background chart surfaces with the BYK-Gardner color meter described above. In addition to reporting the L*, a*, and b* parameters, the meter also calculates ΔE*, the overall change in these color parameters vs. the initial value for each tinted paint sample.

The data are shown in Table 4.

TABLE 4

Paint performance and amine properties for AMP and TA-ACyHM in low-VOC Semi-gloss latex paint

| Paint properties | AMP-95 [1] | TA-ACyHM [2] |
|---|---|---|
| pH, 1 day | 9.47 | 9.32 |
| 1 week @ 60° C. | 9.18 | 8.99 |
| 4 weeks @ 60° C. | 8.87 | 8.60 |
| viscosity (KU), 1 day | 89 | 86 |
| 4 weeks @ 60° C. | 86 | 83 |
| ICI viscosity (P), 1 day | 0.85 | 0.88 |
| 1 week @ 60° C. | 0.73 | 0.74 |
| % opacity, 1 day | 98.07 | 97.98 |
| 4 weeks @ 60° C. | 97.30 | 97.51 |
| yellowness (b* parameter), 1 day | 1.95 | 1.91 |
| 4 weeks @ 60° C. | 1.90 | 2.17 |
| Gloss, 60° initial (1 or 2 days) | 44.8 | 48.1 |
| 1 week @ 60° C. | 38.1 | 45.7 |
| Scrub resistance, delta % relative to AMP | reference | −25% |
| Wet adhesion, 1 day dry, % removal after 500 cycles | 0% | 0% |
| Blocking resistance, 1/3 days cure Apply 1 kg weights, 30 minutes @ 50° C. | 5/6 | 5/5 |
| Color Acceptance: Tinted with phthalo blue and rolled 7 days: delta-E* vs. initial | 0.56 | 0.39 |

[1] Comparative compound.
[2] Compound of the invention prepared as described in above.

As can be seen from the data in Table 4, except for scrub resistance, the TA-ACyHM formulation performs comparably to the AMP in a low VOC formulation, with slight improvement in gloss and marginal improvement in color stability. The TA-ACyHM formula has the further advantage of negligible odor, thus addressing the concern of amine odor in low-VOC paint formulations. Still further, since TA-ACyHM has essentially zero VOC contribution, the formulator has more flexibility to improve paint properties that are usually obstacles in low-VOC formulation, such as open time and freeze-thaw stability, while still meeting the low-VOC definition.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A compound of formula (I):

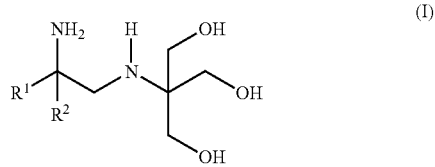

wherein $R^1$ and $R^2$ are independently $C_1$-$C_{10}$ alkyl, or $R^1$ and $R^2$, together with the carbon to which they are attached, form a $C_3$-$C_{12}$ cycloalkyl ring optionally substituted with $C_1$-$C_6$ alkyl.

2. A compound according to claim 1 wherein $R^1$ is $C_1$-$C_3$ alkyl.

3. A compound according to claim 1 wherein $R^2$ is $C_1$-$C_3$ alkyl.

4. A compound according to claim 1 wherein or $R^1$ and $R^2$, together with the carbon to which they are attached, form a $C_5$-$C_8$ cycloalkyl ring.

5. A compound according to claim 1 selected from: 2-(2-amino-2-methylpropylamino)-2-(hydroxymethyl)propane-1,3-diol, and 2-((1-aminocyclohexyl)methylamino)-2-(hydroxymethyl)propane-1,3-diol.

6. An aqueous based paint or coating comprising a neutralizing agent, a binder, a carrier, and a pigment, wherein the neutralizing agent is a compound of claim 1.

7. An aqueous based paint or coating according to claim 6 further comprising one or more additional ingredients selected from: leveling agents, surfactants, thickeners, rheology modifiers, co-solvents, corrosion inhibitors, defoamers, co-dispersants, additional aminoalcohol compounds, and biocides.

8. An aqueous based paint or coating according to claim 6 wherein the binder is a latex binder.

9. An aqueous based paint composition according to claim 8 wherein the latex binder is an acrylic, vinyl acrylic, styrenated-acrylic, or vinyl acetate ethylene based material, or mixtures of two or more thereof.

10. A method for reducing the volatile organic compound content of an aqueous based paint or coating that contains a neutralizing agent, a binder, a carrier, and a pigment, the method comprising using as the neutralizing agent an effective amount of a compound of claim 1.

* * * * *